(12) United States Patent
Sinues et al.

(10) Patent No.: US 9,121,844 B1
(45) Date of Patent: Sep. 1, 2015

(54) METHOD TO ANALYZE AND CLASSIFY PERSONS AND ORGANISMS BASED ON ODOR PATTERNS FROM RELEASED VAPORS

(75) Inventors: Pablo Martinez-Lozano Sinues, Madrid (ES); Juan Fernandez De la Mora, New Haven, CT (US)

(73) Assignee: Sociedad Europea de Analisis Diferencial de Movilidad, Madrid (ES)

( * ) Notice: Subject to any disclaimer, the term of this patent is extended or adjusted under 35 U.S.C. 154(b) by 278 days.

(21) Appl. No.: 12/556,247

(22) Filed: Sep. 9, 2009

Related U.S. Application Data

(60) Provisional application No. 61/191,520, filed on Sep. 9, 2008.

(51) Int. Cl.
*G01N 33/497* (2006.01)
*G01N 27/62* (2006.01)

(52) U.S. Cl.
CPC ............ *G01N 33/497* (2013.01); *G01N 27/624* (2013.01)

(58) Field of Classification Search
CPC .............. G01N 27/622; G01N 27/624; G01N 30/7266; G01N 30/72; G01N 33/497; H01J 49/165; H01J 49/02; H01J 49/10; H01J 49/145; A61B 5/082
USPC .......................................... 250/281–300, 910
See application file for complete search history.

(56) References Cited

U.S. PATENT DOCUMENTS 3,742,213 A * 6/1973 Cohen et al. .................. 250/282
6,125,845 A * 10/2000 Halvorsen et al. ........ 128/200.24
6,537,802 B1 * 3/2003 Alocilja et al. ............ 435/287.5
6,981,947 B2 * 1/2006 Melker ......................... 600/532
7,047,829 B2 * 5/2006 Napoli ........................ 73/864.31
(Continued)

FOREIGN PATENT DOCUMENTS

WO    WO 2007082941 A1 *  7/2007

OTHER PUBLICATIONS

Martinez-Lozano P and J. Fernandez de la Mora, "Electrospray ionization of volatiles in breath", Int. J. Mass Spectrometry, 265 (1): 68-72, 2007.*
(Continued)

*Primary Examiner* — Nicole Ippolito
*Assistant Examiner* — Wyatt Stoffa
(74) *Attorney, Agent, or Firm* — Hoffmann & Baron, LLP

(57) ABSTRACT

A rapid method of volatile analysis and interpretation is taught enabling inferences on the surrounding environment as sophisticated as commonly achieved by dogs via olfaction. The method is based on rapid analysis of vapors released by persons or other organisms into a gas, correction of said analysis due to competing ambient volatiles, extraction of abundance patterns of certain preselected metabolites present in said vapor analysis, and classification of said persons or organisms by comparison of said abundance patterns with preestablished standard metabolite patterns. A preferred approach for rapid analysis involves an atmospheric pressure ionization, such as an electrospray cloud, followed by a mass spectrometer with an atmospheric pressure source. A preferred method for background correction is subtraction of the background signal from the sample signal when both are ionized at similar humidity levels. A preferred comparison pattern involves the abundance of fatty acids and other common metabolites. Preferred classification criteria include recognition of individuals, or species, or health state.

13 Claims, 5 Drawing Sheets

(56) References Cited

U.S. PATENT DOCUMENTS

| | | | |
|---|---|---|---|
| 7,355,170 B2 * | 4/2008 | Miller et al. | 250/287 |
| 7,359,802 B1 * | 4/2008 | Lewis et al. | 702/24 |
| 7,364,551 B2 * | 4/2008 | Allen et al. | 600/532 |
| 7,468,672 B2 * | 12/2008 | Harden et al. | 340/573.1 |
| 7,759,065 B2 * | 7/2010 | Koster | 435/5 |
| 7,781,218 B2 * | 8/2010 | Furton et al. | 436/63 |
| 2005/0085740 A1 * | 4/2005 | Davis et al. | 600/532 |
| 2005/0258360 A1 * | 11/2005 | Whitehouse et al. | 250/288 |
| 2006/0289742 A1 * | 12/2006 | Takada et al. | 250/288 |
| 2007/0003980 A1 * | 1/2007 | Woods et al. | 435/7.1 |
| 2007/0003996 A1 * | 1/2007 | Hitt et al. | 435/34 |
| 2007/0044580 A1 * | 3/2007 | Arcas et al. | 73/865.5 |
| 2007/0158543 A1 * | 7/2007 | Clowers et al. | 250/282 |
| 2007/0167853 A1 * | 7/2007 | Melker et al. | 600/532 |
| 2007/0203448 A1 * | 8/2007 | Melker et al. | 604/24 |
| 2007/0258894 A1 * | 11/2007 | Melker et al. | 424/9.1 |
| 2008/0173809 A1 * | 7/2008 | Wu | 250/283 |
| 2008/0210856 A1 * | 9/2008 | Eide et al. | 250/282 |
| 2008/0236249 A1 * | 10/2008 | Fernandez de la Mora | 73/23.35 |
| 2008/0262743 A1 * | 10/2008 | Lewis et al. | 702/19 |
| 2009/0272892 A1 * | 11/2009 | Vertes et al. | 250/282 |
| 2009/0325191 A1 * | 12/2009 | Karpas et al. | 435/7.1 |
| 2010/0003761 A1 * | 1/2010 | Cook et al. | 436/71 |
| 2010/0184178 A1 * | 7/2010 | Beck et al. | 435/167 |
| 2010/0248268 A1 * | 9/2010 | Woods et al. | 435/7.72 |
| 2010/0264304 A1 * | 10/2010 | Pablo et al. | 250/282 |
| 2010/0282962 A1 * | 11/2010 | Machuron-Mandard et al. | 250/282 |
| 2011/0031392 A1 * | 2/2011 | McEwen et al. | 250/283 |
| 2011/0111387 A1 * | 5/2011 | Wu et al. | 435/5 |
| 2011/0313306 A1 * | 12/2011 | Borrajo-Pelaez et al. | 600/532 |
| 2013/0037710 A1 * | 2/2013 | Wu | 250/287 |

OTHER PUBLICATIONS

Dogan, E. B., et al., "Behavioural mode of action of DEET: inhibition of lactic acid attraction" Medical and Veterinary Entomology (1999) 13, 97-100.*

Martinez-Lozano P and J. Fernandez de la Mora, Electrospray ionization of volatiles in breath, Int. J. Mass Spectrometry, 265 (1): 68-72, 2007.*

* cited by examiner

METHOD TO ANALYZE AND CLASSIFY PERSONS AND ORGANISMS BASED ON ODOR PATTERNS FROM RELEASED VAPORS

CROSS-REFERENCE TO RELATED APPLICATION

This application claims the benefit of priority of U.S. provisional patent application 61/191,520 filed on Sep. 9 2008, the entirety of which is incorporated by reference herein.

FIELD OF THE INVENTION

This invention relates to a method to classify organisms, including persons, by rapid analysis and pattern recognition of the composition of the vapors they release to a surrounding gas.

BACKGROUND OF THE INVENTION

There are numerous examples in nature where individuals from various species obtain valuable information relating to other target individuals of their own or a different species, based on volatile substances released to the environment by the target. Such cues may originate from specialized organs, as those producing insect pheromones, or from more common sources such as breath, skin, urine, etc. Mosquitoes, for instance, use $CO_2$ from breath as well as skin volatiles to identify their preys. Many mammals use also urine cues to mark and monitor their territory. Such olfactive information may be used not only to mark territory, find a mate, or locate a prey. Dogs are able to identify concrete individuals based on the sense of smell, and are used by their masters in a great diversity of functions, such as sensing cancers, explosives or drugs.

Key to the success of biological olfaction are the following characteristics:
1) Sensitivity (the ability to sense a particular vapor present at very small concentration);
2) Selectivity (the ability to distinguish the smell of one vapor from that of another, even when the interfering vapor may be far more abundant);
3) Speed (the ability to sense, recognize, and react rapidly to particular vapors and vapor patterns, ideally in real time);
4) Effective pattern recognition strategies.

Humans have attempted to compensate for their relatively poor sense of smell with a range of olfaction devices. Some have been relatively fast, including desorption electrospray ionization DESI (Takáts et al. 2004), its variant extractive electrospray ionization EESI (aimed at ionizing aerosolized samples; Chen et al. 2006) and so called DART (Cody et al. 2005). These approaches have been applied to the study of skin (or membrane in the case of cells or bacteria) substances. For instance Chen et al. (2007) have used a variant of DESI (EESI) to monitor continuously the release of caffeine from the skin of a person before and after drinking three cups of coffee. Song et al. (2007) have monitored DESI ions from intact bacteria. Their observation of acilium ions (acid minus OH) from hexadecanoic and octadecanoic acids is particularly interesting, given the known possibility to distinguish between various species of bacteria based on lipid analysis. Their direct approach is in interesting contrast with conventional bacterial analysis, involving a complex and destructive process of isolation and methylation of membrane fatty acids (Heller et al. 1987; Cole et al. 1991; Marr et al. 1962; Harrington et al. 1989). But these interesting studies have been used primarily to ionize condensed (rather than vapor) samples, and have neither shown high sensitivity to vapor species, nor revealed a particularly rich olfactive pattern from vapors naturally released into the ambient by either persons or other organisms. Relatively rich odor patterns have been observed in volatiles from breath or skin via gas chromatography-mass spectrometry (GC-MS). But GC-MS is not fast, and its most impressive use in skin or breath analysis has required even slower sample collection and preconcentration (Bernier et al. 2000; Gallagher et al. 2008). Another much faster but less sensitive method (in the range of parts-per-billion (ppb); Smith et al. 2005) is so-called selected ion flow tube-mass spectrometry (SIFT-MS). SIFT-MS has provided real-time information on skin emanations on relatively simple molecules of high vapor pressure, such as acetone (Turner et al. 2008). Also, some other relatively light skin species have been detected in vivo with a more sensitive technique (parts-per-trillion, ppt; Lindinger et al. 1998), so-called proton transfer reaction/mass spectrometry (PTR-MS; Steeghsa et al. 2006).

Earlier fast techniques specifically designed to ionize volatiles at atmospheric pressure have been used following pioneering studies based on corona discharges (Lane et al. 1981). An alternative atmospheric charging approach has been based on mixing the vapors of interest with a cloud of small highly charged drops produced by electrospray ionization (ESI). The method, pioneered by Fenn (Whitehouse et al. 1986; Fuerstenau et al. 1999) and Hill (Wu et al. 2000; Tam et al. 2004), and used by Lee and Shiea (1998), has been referred to as secondary ESI (SESI). The inventors herein have used a slight variant of this approach in U.S. patent application Ser. No. 11/732,770, in a charger embodiment where gas is sampled from the ambient, and mixed with the charged cloud of an electrospray of a solvent/buffer relatively free from involatile solutes. U.S. patent application Ser. No. 11/732,770 is incorporated by reference herein in its entirety. Polar volatile species contained in this sampled gas are then ionized, either directly by the charged electrosprayed drops, or by the ions released by evaporation of these drops. The ionized vapors are then analyzed in an atmospheric pressure ionization mass spectrometer (API-MS) or another analytical instrument having an atmospheric pressure source. This approach has been used to analyze human breath in positive ionization (Martínez-Lozano el al. 2007). The method was clearly shown to be fast and sensitive, and revealed relatively complex mass spectra. However, several difficulties arose precluding the observation of sufficiently rich and clearly interpretable olfactive patterns enabling a sophisticated recognition processes (as those occurring in the biological world). One serious difficulty in investigations of dilute vapors in ambient gas is the great number of volatile species present in the atmosphere, even at large distances from any concrete organism. Distinguishing this rich background from the signal vapors originating from the organism is therefore a large part of the problem. Martínez-Lozano et al. (2007) separated the signal and the background by subtracting the mass spectrum obtained from ambient air from that obtained from exhaled air. However, this subtraction method may lead to false results (Martínez-Lozano and Fernández de la Mora. 2008, 2009). Breath has generally a much higher humidity than ambient air, yet, humidity has a large effect on the probability of ionization of many vapors (particularly many of those released by the skin). In order for the mass-spectrum correction to be effective, the background sample needs to be brought to a humidity level similar to that of the real sample. As a result, no prior work has been able to analyze vapors released into the ambient by any organism under the desired conditions matching the sensitivity, selectivity, and speed of sensing and recognizing typical, for instance, of dogs. Either the pattern obtained was rich but the measurement was slow (as in Bernier et al., or Gallhager et al.), or the measurement was fast but the pattern found was either insufficiently rich, or not rapidly interpretable. Accordingly, the purpose of this invention is to provide a means to sense and classify organisms with characteristics comparable to that of the dog, or even better.

SUMMARY OF THE INVENTION

In one embodiment of the invention, the negative SESI-API-MS spectrum of vapors sampled from the atmosphere in the vicinity of the human skin, corrected by subtraction of the similar spectrum from background air, produces rapidly a rich and readily interpretable pattern of ions dominated by many fatty acids and related species, including some with rather low vapor pressure containing up to 18 carbon atoms. The resulting complex but clear series of pairs of numbers (ion mass and signal intensity) is rapidly interpreted by comparison with a previously known pattern to yield the desired recognition. The recognition may be that of a concrete individual for security purposes (as in U.S. patent application Ser. No. 12/008,186 by Gonzalo Fernandez de la Mora), or may relate to the state of health of a person. U.S. patent application Ser. No. 12/008,186 is incorporated by reference herein in its entirety.

In another related embodiment of the invention, what is interpreted to produce a desired recognition is the negative SESI-API-MS spectrum of vapors in human breath, corrected by subtraction of the similar spectrum from humidified background air.

In other related embodiments, positive ionization spectra are analyzed, and patterns of amines or other related species rather than fatty acids are used for interpretation. In other embodiments, other analyzers are used, with or without a mass spectrometer. In others, the air is sampled from the vicinity of other living organisms. Still in others, the recognition relates to dead persons or organisms (whose rather different distinct odor patterns are often recognized by dogs), or to specially fed or treated organisms, basing the recognition process on their time-dependent response to such foods or treatments. For instance, different species of bacteria can be distinguished based on their fatty acid content. Cells or bacteria naturally release vapors enabling certain kinds of direct olfactive classifications. But the intensity of such emissions can be increased by active stimuli. This includes the partial destruction of the bacterial or cellular membrane, as often practiced in existing protocols for bacteria recognition, whereby the rapid olfactive method taught here would be based on the vapors released by such cells or bacteria after suitable treatment. This treatment, however, does not necessarily require destruction of the organism, as different bacteria produce rather different odor patterns while feeding on the same product (during cheese aging, for instance). The terms classification or recognition are used in this invention very broadly, to include classifying humans as well as other organisms, according to such broad criteria as species, health, personal identity within one species, or circumstantial characteristics such as ingestion or contact with dangerous or illegal materials, etc.

DETAILED DESCRIPTION OF THE INVENTION

Figure 1:
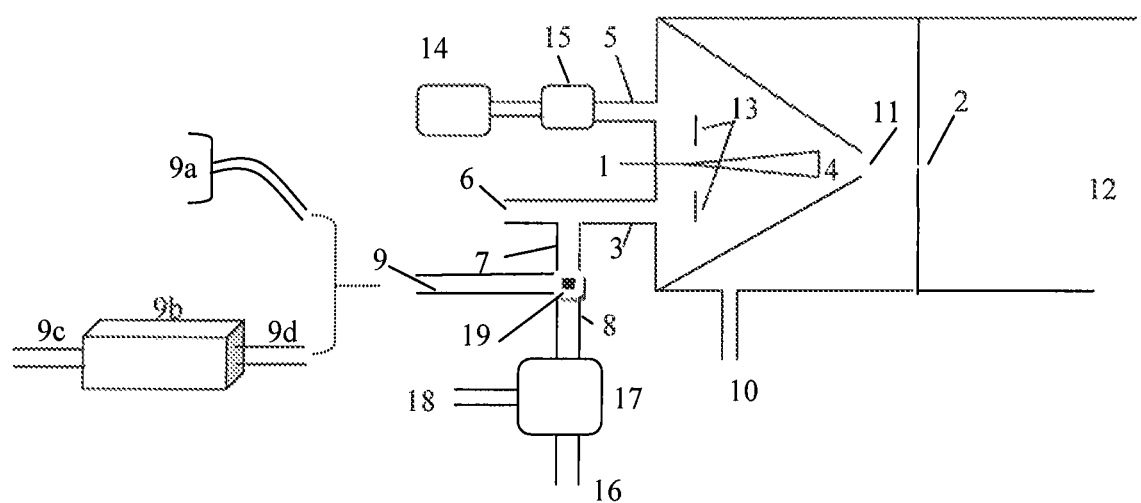
FIG. 1 is a schematic of the SESI ionizer.

A first embodiment of the invention uses a SESI charger (also referred to as an ionizer) interfaced to an API-MS (API mass spectrometer) for breath analysis. This is shown schematically in FIG. 1, which improves upon the arrangement of U.S. patent application Ser. No. 11/732,770 in two key respects: (i) the charger operates now in negative polarity to promote ionization of fatty acids and related vapors, and (ii) the background spectrum (to be subtracted from the breath spectrum in order to provide a signal more directly representative of breath) is obtained from ambient air after bringing it to near 100% relative humidity.

We have used a variety of API mass spectrometers for rapid analysis of breath, including Sciex's API 365 triple quadrupole, and Sciex's Qstar time of flight mass spectrometer. The use of these and other API mass spectrometers with similar SESI sources also in negative mode for explosive detection yields comparable results Martinez-Lozano et al. (2009). Many other API MS systems are commercially available and many others have been fabricated ad hoc by those familiar with the field. Most of them can be readily coupled to a SESI ionizer for practicing the subject invention. The ionization source of FIG. 1 includes an electrospray (ES) capillary 1 facing the MS (mass spectrometer) sampling orifice 2. Neutral vapors enter the chamber through an inlet tube 3 and are forced to pass through a negative electrospray (ES) plume 4. A preferred electrospraying solution to ionize weak acids in negative mode uses 0.1% $NH_4OH$ in 1:1 methanol/water (v/v), obtaining deprotonated vapors (molecular weight minus 1 Da). A variety of other buffers can be used to produce negative ions.

A sample flow rate in the range from 2-8 L/min with a preferred value of 6 L/min is driven in and out of the charging chamber with a source of negative pressure 14, such as a suctioning pump, connected to a second outlet tube 5. This flow is a mixture of a small flow (typically 0.5 L/min) of $CO_2$ (which helps avoiding electrical discharges with negative ES, but is not strictly necessary) entering through inlet 6 and 1.5-7.5 L/min of air entering through branch 7, which is either humidified ambient laboratory air coming through branch 8, or breath coming through branch 9. Some of the vapor molecules carried by the flow entering through line 3 are ionized by the charged drops (or by solution ions released from the drops) in spray 4, are driven by the electric field against a stream of dry counterflow gas fed through line 10 and exiting into the electrospray chamber through orifice 11, and sucked together with approximately 0.5 L/min of dry counterflow gas into the MS 12 through sampling orifice 2. The electric field driving the ions through 11 against the drying gas may be simply created by the electrospray needle, but also with the help of auxiliary electrodes 13. These ions are finally "weighed" in the MS, which determines a signal intensity and an ion mass for each ion or for a desired subgroup of selected ions.

In one approach the breath sample is taken by sealing the sampling tube 9 with the lips and letting the suctioning pump 14 connected to the outlet tube 3 sample the gas from the lungs without opposing any resistance or forcing it in, so that the pressure is almost identical to atmospheric pressure, and the flow rates of sample and background are also almost the same (as seen directly in flowmeter 15). In another approach, the sampling tube 9 is open to the atmosphere in the vicinity of the mouth, and breath is directed into the tube inlet during exhalation. Care must be exerted when handling the sampling tube 9 to avoid contamination coming from the skin. Although wearing gloves is a common approach to control this contamination, note that many plastic gloves are themselves a source of contaminating volatiles. A preferable approach is to fix the sampling tube 9 and avoiding contact with it, or at least restricting contact to portions of the sampling tube 9 sufficiently separated from its sampling end. Preferably the breathing subject fasts overnight to minimize interferences coming from the mouth and obtain a repeatable breath pattern. Samplings without this precaution are also useful to observe the interferences associated to eating.

Figure 2:
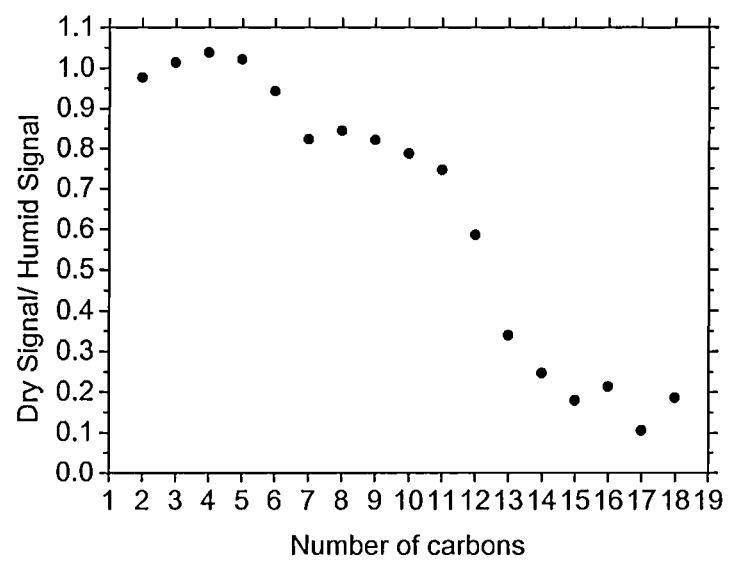
FIG. 2 shows the effect of humidity on the mass spectrometer signal for the series of saturated fatty acids.
Figure 3:
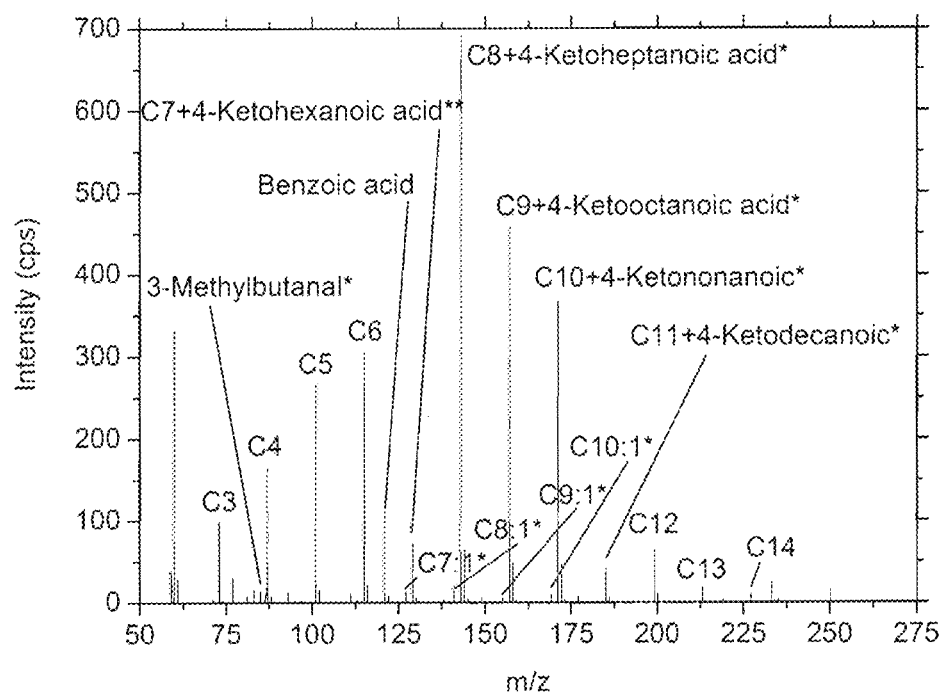
FIG. 3 shows a mass spectrum of human breath corrected by subtraction of the analogous spectrum from the background (previously humidified)

Exhaled breath consists of vapors previously inhaled from the ambient, with some additions and subtractions made in the lung. Accordingly, one must discriminate between endogenous vapors coming from the subject and exogenous vapors originally in the atmosphere. It is important to note that simple subtraction of the mass spectra obtained from either breath or ambient air is often inappropriate to correct for the background, because humidity from breath drastically affects the ionization efficiency (hence the output signal) of many vapors. FIG. 2 represents the ratio of ion signals obtained for saturated fatty acid vapors charged in the setup of FIG. 1 in either dry or humid air, as a function of the number of carbon atoms in the fatty acid molecule. Note the almost tenfold increase in the charging probability of large chains in humid air. As a result, the large fatty acids produced by human skin and contained in the laboratory background are more highly charged when first humidified by passing them through the lung than when drawing them directly from the dry ambient. Simple background subtraction therefore gives the incorrect appearance that breath contains large fatty acids. Consequently, our blank is preferably based on humidified room air and is taken every time immediately before the breath sample. In this way, by simply substituting humid room air spectra from breath spectra, we preserve the detection probability of background contaminants as well as breath metabolites. In the present embodiment of the invention, ambient air entering through line 16 is humidified in chamber 17 prior to entering into the ionization chamber. Humidification can be achieved in a number of well known ways. In one embodiment the humidification chamber 17 is a passive device containing distilled water at 37° C., while ambient air passes through the headspace above the water pool. In another common embodiment, a well controlled flow of distilled water is injected with a syringe pump through port 18 into humidification chamber 17. In this approach one must ensure that the humidification chamber 17 provides complete evaporation of the water fed through 18, and effective mixing of the resulting water vapor with the gas flow coming through 16. This has been previously achieved in work by Zhan and Fenn (2002) by spraying the liquid into very small drops which evaporate immediately into the heated gas. Similar results are reported by Sgro and de la Mora (2004) by heating sufficiently the injected liquid and the gas. Many other variants have been reported, including that used by Martinez-Lozano et al. (2009), who inject controlled quantities of explosive vapor from a solution into a gas, where the injected liquid solution was electrosprayed into particularly small drops, and the gas was also heated to promote complete evaporation. As already noted, the mass spectrometer uses a dry stream of curtain gas flow, entering through line 10 and meeting the electrospray plume frontally after passing through orifice 11. This dry stream precludes penetration of neutral vapors into the analyzer, and handles the high humidity in these samples with no apparent interference of hydrated peaks. Note that this technique is online and requires no sample preparation. The sampling tube 9 is continuously drawing room air at a fixed flow rate, and the subject needs only to exhale in it. Selection between sampling from either the subject's breath (or dry ambient air) through line 9 or sampling humidified ambient air through line 16 is accomplished by a two-way valve 19. A background-corrected mass spectrum obtained by taking the difference between sample and humidified laboratory air is shown in FIG. 3. Among the dominant peaks in the spectrum one sees a series spaced by 14 Da, clearly associated to $CH_2$ addition in a hydrocarbon chain. The series starts with a weak peak at 73 Da, corresponding to deprotonated propionic acid (C3). Its structure was confirmed by its exact mass combined with collision induced dissociation (CID) of the parent ion into several characteristic product peaks. The series continues uninterrupted with well-defined peaks up to deprotonated tetradecanoic acid (myristic; C14). Larger fatty acid chains are contained in the background at concentrations larger than in breath as a result of contamination from skin vapors of persons in the laboratory. This competition makes it difficult to determine small breath concentrations of larger fatty acid by the approach described. However, larger fatty acids can still be quantified if the subject inhales clean bottled air instead of atmospheric air. When applicable, this alternative method of reducing the background is also useful, an is included within the invention. Along with the fatty acids, the high resolution of the time of flight (TOF) MS instrument used cleanly resolves another series of peaks slightly lighter, starting with pyruvic acid and ending at 185 Da. This series most likely corresponds to ketomonocarboxylic acids, according to their exact mass (besides the positive identification by CID of pyruvic and 4-ketohexanoic acid). Note that the breath signal exceeds the background only from 129 Da (4-ketohexanoic acid) to 185 Da (4-ketodecanoic acid). The particular position of the keto group has not been confirmed by alternative procedures and could be different. Interestingly, 2-ketohexanoic acid is a known potent insulin secretagogue (Lenzen et al. 1982). Benzoic acid (121 Da) is also present, as confirmed by CID. 3-Methylbutanal (85 Da) has been tentatively identified, and some other minor peaks may be also aldehydes according to their exact mass. For instance, butanal (71 Da); 3-methylbut-2-enal (83 Da); 3-hexenal (97 Da; related to R-linolenic acid metabolism); 4-methylpentanal (99 Da); and heptanal (113 Da). We also observe a series of peaks displaced 2 Da to the left of the main saturated fatty acid series. On the basis of their exact mass, they correspond most probably to singly unsaturated fatty acids: C7:1 (127 Da), C8:1 (141 Da), C9:1 (155 Da), and C10:1 (169 Da). Longer chains up to C18:1 are observed in the background at concentrations higher than in breath. The dominant background peak at 89 Da corresponds to 2-hydroxypropanoic acid (lactic acid), secreted in bulk quantities by the skin. However, we observe 2-hydroxyhexanoic acid (131 Da), 2-hydroxyheptanoic acid (145 Da), and 2-hydroxyoctanoic acid (159 Da) clearly above the background level (assigned only by their exact mass).

In conclusion, the method of analysis described yields a large number of peaks in breath, many of which are associated to known human metabolites, and can be differentiated from the background. Unlike prior art, the approach therefore has all the outstanding characteristics of biological detectors. A preferred method for classification of persons would therefore extract from a spectrum such as that shown in FIG. 1 a list of the n abundances of certain pre-established metabolite ions. The associated n-dimensional vector characteristic of that person can be compared with a reference vector to achieve a match or a mismatch. Many techniques exist to perform the comparison between a pattern and one or many reference standards, some of which account through training for the variability of the fingerprint. This variability could in our case be due to environmental conditions such as cleanness, eating history, etc. There is similarly a variability in the mass spectra produced by electron fragmentation of given molecules, but this does not preclude their identification in existing algorithms (i.e. the NIST MS search software), once the recognition software is suitably trained by being fed the range of mass spectra characteristic of this natural variability. Cristoni et al. (2009) have illustrated the capabilities of this NIST software in the recognition of cancerous vs. healthy mass spectra, showing a better performance than traditional multivariate analysis (clustering and principal component analysis).

We have so far discussed the analysis of human breath. But the invention includes also probing volatiles from other organisms, with small variants that can be readily implemented by those familiar with the field of breath analysis. In one such variation applicable also to humans, a breathing mask 9a may be used to connect the mouth of an animal to sampling line 9 for greater convenience. In this case the two-way valve 19 is removed so that the gas continuously ingested through inlet 3 comes automatically through the path of least resistance, namely, from the animal breath when it exhales, and otherwise from the background line 16. When the animal inhales, a valve in the breathing mask opens widely such that the flow rate of gas entering through 16, requiring efficient humidification, does not increase substantially above the flow sample through line 3 when the animal is not breathing. Depending on the size of the animal, the volume sampled through inlet line 3 would have to be adjusted. The term breath should in some cases be understood broadly. For instance, metabolites released by a colony of organisms, such as a cellular colony, may be evaluated. For example, when analyzing the metabolites released by a colony of organisms residing (for instance) on a fermenting piece of cheese, the distinction between vapors released from either breath and skin (or membrane) is lost, but the method can still be used with small modifications. In this case, the colony may be enclosed in a container 9b having an inlet 9c and an outlet 9d, while purified gas (also humidified if appropriate for that organism) would enter through this inlet 9c, circulate through the interior of the container 9b, and carry the vapors released by the colony to the outlet tube 9d connecting to 9 and into the analyzer. Naturally, for a small volume chamber (relative to the volume of the human lung), a flow rate substantially smaller than 6 L/min should be used. For other small animals having distinct breathing organs, it may be difficult or impractical to distinguish between vapors released from the lungs or from other organs, in which case, placing the animal in the container 9b (similarly to the case of the colony just discussed) and sampling the vapors released from organs other than the lungs (perhaps including also urine and faeces) is equally appropriate and is included within the invention. Metabolites originating from a fish tank (or a cell culture) residing in water can similarly be sampled and analyzed by passing the sampling gas through the headspace above this water.

Figure 4:
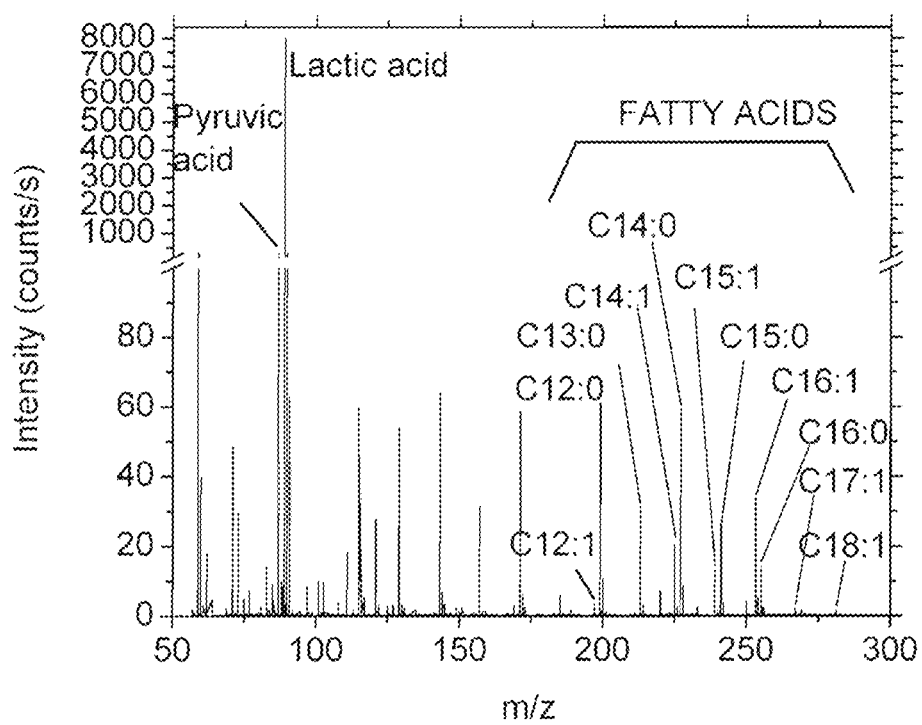
FIG. 4 shows a mass spectrum of ambient air sampled from the vicinity of a human hand, corrected by subtraction of the spectrum from the background.

In a second embodiment of the invention using the same instrument as in the prior embodiment, cutaneous vapors are analyzed. The sample is now drawn by locating the open end of line 9 in the vicinity of the human skin (for instance the palm of the hand). This embodiment can also be used with other organisms via slight variations, as just discussed for breath, whereby the term skin is also used broadly to include various organisms, for instance the cellular membrane or the leaf of a plant. In one embodiment the background air is drawn also from the atmosphere through the open end of line 9, placing it at a safe distance from any individual. In this case, the level of humidity in the vicinity of the hand is not greatly affected by the hand, so, humidification of the background is not essential. However, humidification of both the sample and the background is a useful possibility that not only provides a better humidity control, but also enhances considerably the sensitivity towards long chain fatty acids (FIG. 2). To achieve this benefit, both the sample and the room background are drawn in sequence (first one, then the other) into the mass spectrometer through line 16. For this measurement valve 19 would only admit gas coming through 8. A background-corrected mass spectrum obtained for human skin in negative mode is shown in FIG. 4, with more details provided by Martinez-Lozano and Fernandez de la Mora 2009. FIG. 4 shows that such skin spectra are as well suited for classification or recognition purposes as that shown in FIG. 3 for breath. Some particularly notable features of human skin spectra are the presence of long chain fatty acids up to at least oleic acid (C18:1), and the singular intensity of lactic acid, and to a lesser extent pyruvic acid (notice the break in the scale introduced in FIG. 4 to enable representing these high abundances). The extraordinary signal obtained for lactic acid suggests its use for simple detection of the presence of humans in closed controlled areas, or for related search purposes. Note also that pyruvic acid is known to be involved in type II diabetes mellitus metabolism. The skin spectrum of FIG. 4 includes the complete series of saturated fatty acids from C12:0 to C16:0, as well as unsaturated fatty acids from C12:1 to C18:1. Other abundant metabolites are Pyruvaldehyde, Glyoxylic acid, 4-Hydroxybutanoic acid; 3-Methyl-2-oxobutanoic acid; 5-Hydroxypentanoic acid and 4-methyl-2oxopentanoic acid. Fatty acids smaller than C12 surely originate also from the skin, but their presence is difficult to measure in the open atmosphere method described due to competition from more abundant light fatty acids originating from the breath of persons in the laboratory. This is the converse problem to the one previously described in relation to the detection of heavy fatty acids from breath. A variety of cleaning strategies can similarly be adopted here to avoid or reduce background contamination from breath and enable determination of lighter skin fatty acids. The most informative strategy involves obtaining separate mass spectra for both the skin and breath, since the corresponding metabolites have different origins and therefore provide independent pieces of intelligence. Breath provides a window into the composition of volatile species dissolved in the bloodstream, while many skin volatiles are also influenced by the activity of skin bacteria. Several hundred distinct skin fatty acids exist in the human skin (Nicolaides 1974) offering an incredibly rich fingerprint. Many of these species are isomers having exactly the same mass. But even isomers may often be distinguished by suitable analytical techniques, including the combination between an ion mobility spectrometer (for instance, a differential mobility analyzer, DMA) and a mass spectrometer.

Figure 5:
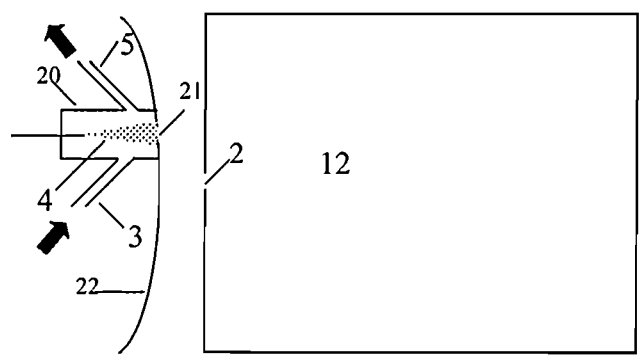
FIG. 5 shows an instrument for analyzing ambient vapors, including the charger of FIG. 1, a differential mobility analyzer and a mass spectrometer.

FIG. 5 shows a schematic of such an embodiment. Target vapors enter into an ionization chamber 20 through inlet tube 3. Said vapors are sampled into the chamber by applying suction through a small pump connected to the exit port 5. The sampled gas gets in contact with the electrospray cloud 4, some of its vapor components become ionized and are then driven by the prevailing electric field against a clean curtain gas flow coming from the DMA through orifice (slit) 21 located at the left DMA electrode 22. These ions are classified according to their electrical mobility within the DMA, with the help of an auxiliary flow of clean gas moving vertically. As a result, only those ionized vapors within a narrow range of mobilities proceed into the exit DMA sample orifice leading directly to the inlet orifice 13 to the mass spectrometer 12. Because the various fatty acid isomers have different electrical mobilities, the DMA-MS combination can distinguish a larger number of such vapors than the MS alone. A more detailed description of the coupling of a DMA and a MS is given in U.S. patent application Ser. No. 11/786,688 by Juan Rus et al. U.S. patent application Ser. No. 11/786,688 is incorporated by reference herein in its entirety.

The work described has demonstrated the ability to detect vapor chains including up to 18 carbon atoms. Even heavier vapors are known to be part of the skin spectrum and may be similarly detected in more sensitive mass spectrometers, such as modern triple quadrupoles. Also included in the invention are alternative sampling methods previously used in skin analysis via GC-MS. In one approach (slightly slower than direct sampling from the atmosphere, but must faster than GC-MS) a cotton with a solvent such as ethanol briefly touches the skin. This cotton is inserted into a small chamber and heated above body temperature to release low volatility vapors conveyed through heated lines to the same SESI-DMA-APIMS device previously described.

The methods described admit many variants considered also part of this invention. For instance, clean, rich and readily interpretable spectra containing numerous metabolites (such as amines) are obtained in the embodiment of figure with positive electrospray ionization, as discussed in more detail by Martinez-Lozano (2009) in the case of cutaneous vapors. Volatiles released from the headspace above other body fluids can similarly be analyzed to provide complementary classification criteria. For instance, Martinez-Lozano (2008) has examined the volatiles from urine and found a number of metabolites different from those produced by breath or skin. We also note that recent nuclear magnetic resonance (NMR) metabolic studies on urine have shown that, in spite of temporal variabilities (e.g. biochemical cycles, diet, etc.), a stable metabolic fingerprint strongly individual-specific exists (Assfalg et al. 2008; Holmes et al. 2008), even at timescales as long as 3 years (Bernini et al. 2009).

The electrospray ionizer described here has numerous advantages, but useful spectra can also be obtained with alternative chargers. For instance, passing the sample gas through the interior of a metal tube coated with 10 milliCurie of $Ni^{63}$ produces a spectrum from breath or skin containing a similar number of fatty acids as the SESI ionizer. Other alternative geometries and radioactive source intensities would also be useful, as would other chargers commonly used for atmospheric pressure ionization. The tests described have involved persons, but other individual organisms or colonies of organisms can be similarly probed and classified.

Some comment is finally appropriate regarding the immense range of different criteria or purposes for which one would wish to analyze and classify different organisms according to the present invention. Nature provides numerous examples of the practical benefits that an improved sense of smell would bring to our own species. Some additional particularly interesting examples are provided by the interaction between the dog and his human master (besides the dog's capacity to distinguish different concrete persons by their scent). For instance, the dog has demonstrated an ability to sniff various human cancers, often with great accuracy, sometimes at an early stage at which no other detection means are known (Church and Williams 2001; Welsh et al. 2008). Also, anecdotal reports suggest that some dogs can provide early warning of hypoglycemia episodes by 'sniffing' their owner's dropping blood sugar levels. These observations show that not only individual persons, but also their state of health often have distinct volatile signatures. These states of health can therefore be classified according to the present invention. Another important fact to be noted is that dogs are often claimed to be sensitive to parts per trillion (ppt) concentrations of certain vapors (Walker et al., 2006), while SESI-API-MS has already shown a substantially better sensitivity.

REFERENCES CITED

Assfalg M, Bertini I, Colangiuli D, Luchinat C, Schäfer H, Schütz B, Spraul M. Proc Natl Acad Sci USA. 2008, 105 (5), 1420-4.

Bernier U R, Kline D L, Barnard D R, Schreck C E, Yost R A. *Anal. Chem.* 2000; 72: 747

Bernini P, Bertini I, Luchinat C, Nepi S, Saccenti E, Schäfer H, Schütz B, Spraul M, Tenori L. J Proteome Res. 2009, 10.1021/pr900344m Chen H, Venter A, Cooks R G. *Chem. Commun.* 2006; 2042

Chen H, Yang S, Wortmann A, Zenobi R. *Angew. Chem. Int. Ed.* 2007; 46: 7591

Church J, Williams H. *Lancet* 2001; 358: 930.

Cody R B, Laramee J A, Durst H D. *Anal. Chem.* 2005; 77 (8): 2297

Cole M J, Enke C G. *Anal. Chem.* 1991; 63: 1032.

Cristoni, S. Molin, L. Lai, A. Bernardi, L. R. Pucciarelli, S. Agostini, M. Bedin, C. Nitti, D. Seraglia, R. Repetto, O. Dibari, V. F. Orlandi, R. Martínez-Lozano, P. Traldi, P. Rapid Commun. Mass Spectrom. 2009, 23, 1.

Fuerstenau S, Kiselev P, Fenn J B. *Proc. 47th ASMS Conf. Mass Spectrom. Allied Topics*; Dallas (Tex.) USA June, 1999 (ThOE 3:00).

Gallagher M, C. J. Wysocki, J. J. Leyden, A. I. Spielman, X. Sun, G. Preti. British Journal of Dermatology, Early View, published online 14 Jul. 2008. DOI: 10.1111/j.1365-2133.2008.08748.x Harrington P B, Street T E, Voorhees K J, Brozoo F R, Odom R W. *Anal. Chem.* 1989; 61: 715.

Heller D N, Cotter R J, Fenselau C, Uy O M. *Anal. Chem.* 1987; 59: 2806.

Holmes E, Loo R L, Stamler J, Bictash M, Yap I K, Chan Q, Ebbels T, De Iorio M, Brown Lane, D. A.; Thomson, B. A. Monitoring a Chlorine Spill from a Train Derailment. *J. Air Pollution Control Assoc.* 1981, 31(2), 122-127.

Lee C Y, Shiea J. *Anal. Chem.* 1998; 70: 2757.

Lenzen, S.; Formanek, H.; Panten, U. *J. Biol. Chem.* 1982, 257 (12), 6631-6633.

Lindinger W, Hansel A, Jordan A. *Int. J. Mass Spectrom. Ion Proc.* 1998; 173: 191

Marr A G, Ingraham J L. J. Bacteriol. 1962; 84, 1260.

Martínez-Lozano P. *Proc. 56th ASMS Conf. Mass Spectrom. All. Top.* 2008, Denver, Colo. (WP 517).

Martinez-Lozano P, Mass spectrometric study of cutaneous volatiles by secondary electrospray ionization, Int. J. Mass Spectrom. 282(3) 128-132, 2009

Martínez-Lozano P and J. Fernández de la Mora, Electrospray ionization of volatiles in breath, Int. J. Mass Spectrometry, 265 (1): 68-72, 2007

Martinez-Lozano P and J. Fernández de la Mora, Detection of fatty acid vapors in human breath by atmospheric pressure ionization mass spectrometry, Analytical Chemistry, 2008, 80 (21), 8210-8215

Martinez-Lozano P and J. Fernández de la Mora, Direct mass spectrometric analysis of human skin vapors charged by secondary electrospray ionization, J. Am. Soc. Mass Spectrom, 20, 1060-1063, 2009

Martinez-Lozano P, J. Rus, G. Fernández de la Mora, M. Hernández, J. Fernández de la Mora, Secondary Electrospray Ionization (SESI) of Ambient Vapors for Explosive Detection at Concentrations Below Parts Per Trillion. J. Am. Soc. Mass Spectr. 2009, 20, 287-294

Nicolaides N. *Science* 1974; 186 (4158): 19.

Sgro L A and J. Fernandez de la Mora, A Simple Turbulent Mixing CNC for Charged Particle Detection Down to 1.2 nm, Aerosol Science and Technology, 38, 1-11, 2004

Smith D, Španeĺ P. *Mass Spectrom. Rev.* 2005; 24 (5): 661.

Song Y, Talaty N, Tao W A, Pan Z, Cooks R G. *Chem. Commun.* 2007; 61.

Steeghsa M M L, Moeskopsa B W M, van Swama K, Cristescua S M, Scheepersb P T J, Harren F J M. *Int. J. Mass Spectrom.* 2006; 253: 58

Takáts Z, Wiseman J M, Gologan B, Cooks R G, *Science* 2004; 306: 471.

Tam M, Hill H Jr. *Anal. Chem.* 2004; 76 (10): 2741.

Turner C, Parekh B, Walton C, Španeĺ P, Smith D, Evans M. *Rapid Comm. Mass Spectrom.* 2008; 22 (4): 526.

Veselkov I J, K A, Daviglus M L, Kesteloot H, Ueshima H, Zhao L, Nicholson J K, Elliott P. Nature 2008, 453 (7193), 396-400

Walker D B, Walker J C, Cavnar P J, Taylor J L, Picket D H, Hall S B, Suarez J C. *Appl. Anim. Behav.* Sci. 2006; 97 (2-4): 241.

Welsh J S, Barton D, Ahuja H. *Comm. Oncol.* 2005; July/August: 324.

Whitehouse C M, Levin F, Meng C K, Fenn J B. *Proc.34th. ASMS Conf Mass Spectrom. Allied Topics*, Denver (Colo.) USA, 1986, p. 507.

Wu C, Siems W F, Hill H Jr. *Anal. Chem.* 2000; 72: 396.

Zhan D L, Fenn J B, Source: Gas phase hydration of electrospray ions from small peptides, Int. J. Mass Spectr. 219(1) 1-10, 2002

What is claimed:

1. A method to analyze metabolites released by at least one organism, said method including the following steps:
   sampling into an ionizer containing anions a sample flow of gas after bringing it in contact with said at least one organism, such that said gas carries sample vapors released by said at least one organism, said ionizer converting at least some of said sample vapors into negative ions by transfer of charge between said anions and molecules of said vapors;
   introducing said ions into an analytical instrument having an atmospheric pressure ion source to determine relative ion abundances;
   determining from said relative ion abundances a sample list of relative abundances for a pre-established group of metabolite ions;
   sampling into an ionizer a background flow of said gas without bringing it in contact with said at least one organism, said gas carrying background vapors, said ionizer converting at least some of said background vapors into background ions;
   determining a background list of relative abundances, based on said background ions, for said pre-established group of metabolite ions when said gas carrying said background vapors is ingested by said analytical instrument; and
   determining a background-corrected list of relative abundances for said pre-established group of metabolite ions by subtracting said background list from said sample list,
   wherein, said analytical instrument includes either a differential mobility analyzer or a mass spectrometer,
   wherein, said sample vapors are not prepared prior to being sampled into said ionizer, and,
   wherein, at least one among said background flow of said gas and said sample flow of said gas are humidified prior to being sampled into said ionizer.

2. A method to classify at least one organism according to claim 1, further comprising comparing said background-corrected list of relative abundances for said pre-established group of metabolite ions with at least one reference list of metabolite ion concentrations.

3. The method according to claim 1 where an external stimulus is applied to enhance the release of said vapors from said organisms.

4. The method according to claim 3 where said at least one organism are bacteria and said external stimulus involves supplying said bacteria with at least one nutrient.

5. The method according to claim 1 where said pre-established group of metabolite ions are selected from the classes of organic acids, ketocarboxylic acids, aldehydes, ketones, amines, and combinations thereof.

6. The method according to claim 1 where said at least one organism are bacteria or cells.

7. The method according to claim 1 where said at least one organism are human persons.

8. The method according to claim 2 where said classification involves identification of a specific person.

9. The method according to claim 2 where said classification relates to the health of a person.

10. The method according to claim 1 where at least one among said organisms is dead.

11. The method of claim 1 where said ionizer includes an electrospray cloud.

12. A method to analyze metabolites released by at least one organism, said method including the following steps:
   i) sampling into an ionizer a sample flow of gas after having it in contact with said at least one organism, such that said gas carries sample vapors released by said at least one organism, said ionizer converting at least some of said sample vapors into sample vapor ions;
   ii) humidifying a background flow of said gas which is not brought into contact with said at least one organism, said background flow of gas carrying background vapors;
   iii) sampling into said ionizer or an alternative ionizer said humidified background flow of gas, said ionizer converting at least some of said background vapors into negative ions;
   iv) introducing said sample vapor ions into an analytical instrument having an atmospheric pressure ion source to determine relative ion abundances;
   v) introducing said negative ions into an analytical instrument having an atmospheric ion source to determine relative background ion abundances;
   vi) determining from said relative ion abundances a sample list of relative abundances for a pre-established group of metabolic ions;

vii) determining from said relative background ion abundances a background list of relative abundances for said pre-established group of metabolic ions; and, viii) determining a background-corrected list of relative abundances for said pre-established group of metabolic ions by subtracting said background list from said sample list.

13. The method according to claim 12 further comprising humidifying said sample flow of gas prior to being sampled into said ionizer.

* * * * *

UNITED STATES PATENT AND TRADEMARK OFFICE
CERTIFICATE OF CORRECTION

| | | |
|---|---|---|
| PATENT NO. | : 9,121,844 B1 | Page 1 of 1 |
| APPLICATION NO. | : 12/556247 | |
| DATED | : September 1, 2015 | |
| INVENTOR(S) | : Pablo Martinez-Lozano Sinues et al. | |

It is certified that error appears in the above-identified patent and that said Letters Patent is hereby corrected as shown below:

On the title page item (75) Inventors, replace "Juan Fernandez De la Mora" with --Juan Fernandez de la Mora--.

Signed and Sealed this
First Day of March, 2016

Michelle K. Lee
*Director of the United States Patent and Trademark Office*